(12) United States Patent
Bowlin et al.

(10) Patent No.: US 6,787,357 B2
(45) Date of Patent: Sep. 7, 2004

(54) PLASMA-DERIVED FIBRIN-BASED MATRICES AND TISSUE

(75) Inventors: Gary L. Bowlin, Mechanicsville, VA (US); Gary Wnek, Midlothian, VA (US); David G. Simpson, Mechanicsville, VA (US); Philippe Lam, Richmond, VA (US); Marcus E. Carr, Midlothian, VA (US); Helen Fillmore, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 09/970,651

(22) Filed: Oct. 5, 2001

(65) Prior Publication Data

US 2002/0094514 A1 Jul. 18, 2002

Related U.S. Application Data

(63) Continuation-in-part of application No. 09/654,517, filed on Sep. 1, 2000, now abandoned.

(51) Int. Cl.$^7$ .............................. C12N 5/02; C12N 5/00; C12N 15/87; A61F 2/06
(52) U.S. Cl. ....................... 435/395; 435/325; 435/455; 600/36
(58) Field of Search ................................. 435/395, 325, 435/455; 600/36

(56) References Cited

U.S. PATENT DOCUMENTS

| | | |
|---|---|---|
| 1,975,504 A | 10/1934 | Formhals |
| 4,043,331 A | 8/1977 | Martin et al. ................ 128/156 |
| 4,044,404 A | 8/1977 | Martin et al. ..................... 3/19 |
| 4,657,793 A | 4/1987 | Fisher .......................... 428/36 |
| 5,256,418 A | 10/1993 | Kemp et al. ................. 424/423 |
| 5,292,362 A | 3/1994 | Bass ........................... 106/124 |
| 5,378,469 A | 1/1995 | Kemp et al. ................. 424/423 |
| 5,460,962 A | 10/1995 | Kemp ......................... 435/238 |
| 5,580,859 A | 12/1996 | Felgner et al. ................ 514/44 |
| 5,723,324 A | 3/1998 | Bowlin et al. |
| 5,787,567 A | 8/1998 | Miyazaki ..................... 29/596 |
| 5,906,934 A | 5/1999 | Grande et al. |
| 5,908,777 A | 6/1999 | Lee et al. .................... 435/320 |
| 5,910,488 A | 6/1999 | Nabel et al. .................. 514/44 |
| 5,912,177 A | 6/1999 | Turner ......................... 435/455 |
| 5,935,437 A | 8/1999 | Whitmore ................ 210/321.6 |
| 5,948,654 A | 9/1999 | Tranquillo |
| 6,057,137 A | 5/2000 | Tranquillo et al. .......... 435/174 |
| 6,096,309 A | 8/2000 | Prior et al. .............. 424/94.63 |
| 6,103,255 A | 8/2000 | Levens et al. |
| 6,106,913 A | 8/2000 | Scardino et al. ........... 428/36.3 |
| 6,110,484 A | 8/2000 | Sierra |
| 6,110,590 A | 8/2000 | Zarkoob et al. ............ 428/364 |
| 6,146,892 A | 11/2000 | Ma et al. |
| 6,179,872 B1 | 1/2001 | Bell et al. |
| 6,180,605 B1 | 1/2001 | Chen et al. |
| 6,180,606 B1 | 1/2001 | Chen et al. |
| 6,245,345 B1 | 6/2001 | Swanbom et al. |

OTHER PUBLICATIONS

Torbet, J., "Fibrin Assembly in Human Plasma and Fibrinogen/Albumin Mixtures" (1986) Biochemistry, 25, 5309–5314.*

Tissue Engineered Skeletal Muscle: Preparation of Highly Dense Highly Oriented Hybrid Muscular Tissue, Okano, Cell Transplantation, vol. 7, No. 1, pp. 71–82, 1998.

Regulation of New Blood Vessel Growth Into Ischemic Skeletal Muscle, Bush et al., Journal of Vascular Surgery, vol. 28, No. 5, pp. 919–928, 1998.

Controlled Delivery Of Vascular Endothelial Growth Factor Promotes Neovascularization And Maintains Limb Function In A Rabbit Model of Ischemia, Hopkins et al., Journal of Vascular Surgery, vol. 27, No. 5, pp. 886–895, 1997.

Revascularization Of Skeletal Muscle Transplanted Into The Hamster Cheek Pouch: Electron Microscopy, Weiss et al., Microvascular Research, vol. 26, pp. 65–73, 1983.

Mechanism Of Compensatory Hypertrophy In Skeletal Muscle Of The Rat, Gutmann et al., Experimental Neurology, vol. 31, pp. 451–464, 1971.

Identification Of Self–Renewing Myoblasts In the Progeny Of Single Human Muscle Satellite Cells, Baroffio et al., Differentiation, vol. 60, pp. 47–57, 1996.

Patterned Growth of Neonatal Rat Heart Cells In Culture, Rohr et al., Circulation Research, vol. 68, No. 1, pp. 114–130, 1991.

Cardiomyocyte Transplantation In A Porcine Myocardial Infarction Model, Watanabe et al., Cell Transplantation, vol. 7, No. 3, pp. 239–246, 1998.

Hybrid Muscular Tissues: Preparation of Skeletal Muscle Cell–Incorporated Collagen Gels, Okano et al., Cell Transplantation, vol. 6, No. 2, pp. 109–118, 1997.

Myoblast Seeding In A Collagen Matrix Evaluated in vitro, Wachem t al., Journal of Biomedical Materials Research, vol. 30, pp. 353–360, 1996.

What Are The Residual Stresses Doing in Our Blood Vessels?*, Fung, Annals of Biomedical Engineering, vol. 19, pp. 237–249, 1991.

Mechanical Properties of Synthetic Arterial Grafts*, Hasegawa et al., J. Biomechanics, vol. 12, pp. 509–517, 1979.

Poly(L–lactide): A Long Term Degradation Study In Vivo, Part III, Analytical Characterization, Pistner et al., Biomaterials, vol. 14, No. 4, 1993.

(List continued on next page.)

Primary Examiner—Jon P. Weber
(74) Attorney, Agent, or Firm—John H. Thomas, PC

(57) ABSTRACT

The invention is directed to use of fibrin as an extracellular matrix and, together with cells, its use in forming engineered tissue. The engineered tissue can include the synthetic manufacture of specific organs or "organ-like" tissue. A preferred embodiment is a plasma-derived fibrin matrix containing cells.

15 Claims, 5 Drawing Sheets

OTHER PUBLICATIONS

Chapter 5, Essential Physical Characteristics of Vascular Grafts, Stewart et al., Modern Vascular Grafts, pp. 115–132.
Utilization of Composite Laminate Theory In The Design of Synthetic Soft Tissues for Biomedical Prostheses, Gershon et al., Butterworth–Heinemann ltd., 1990.
Introducing A Selectively Biodegradable Filament Wound Arterial Prosthesis: A Short–Term Implantation Study, Cohn et al., Journal of Biomedical Materials Research, vol. 26, pp. 1185–1205, 1992.
Synthesis And Properties of Biodegradable Polymers Used As Synthetic Matrices For Tissue Engineering, Wong et al., Synthetic Biodegradable Polymer Scaffolds, Chapter 4, pp. 52–82, 1997.
Generation of Polymer Nanofibers Through Electrospinning, Dietzel et al., Army Research Laboratory, Jun. 1999.
Engineering Design of Vascular Prostheses, How et al., Proc Instn Mechn Engrs, vol. 206, pp 61–71, 1992.
Generation of Synthetic Elastin–Mimetic Small Diameter Fibers and Fiber Networks, Huang et al., Macromolecules 2000, 33, 2989–2997, 2000.
Dynamic Mechanical Conditioning of Collagen–Gel Blood Vessel Constructs Induces Remodeling in Vitro, Seliktar et al., Annals of Biomedical Engineering, vol. 28, pp. 351–362, 2000.
Vascular Mechanics, Dobrin, Handbook of Physiology—The Cardiovascular System III.
Relation of Structure to Function of the Tissues of the Wall of Blood Vessels, Burton, Physilogical Reviews, vol. 34, No. 4, Oct. 1954.
Mechanical Stress–Induced Orientation and Ultrastructual Changes of Smooth Muscle Cells Cultured In Three–Dimensional Collagen Lattices, Kanada et al., Cell Transplantation, vol. 3, No. 6, pp. 481–492, 1994.
The Cardiovascular System, Section 2, vol. II, Bohr et al., Handbook of Physilogy, American Physiological Society, 1980.
Functional Arteries Grown in Vitro, Niklason et al., Science, vol. 284, Apr. 16, 1999.
Lab–Grown Organs Begin to Take Shape, Ferber, Science, vol. 284, Apr. 16, 1999.
Creation of Viable Pulmonary Artery Autografts Through Tissue Engineering, Shinoka et al., The Journal of Thoracic and Cardiovascular Surgery, vol. 115, No. 3, pp. 536–546, 1998.
The Degree of Nonlinearity and Anisotrophy of Blood Vessel Elasticity, Zhou et al., Proc. Natl. Acad. Sci. USA, vol. 94, pp. 14255–14260, Dec. 1997.
Mechanical Factors Predisposing To Intimal Hyperplasia And Medial Thickening In Autogenous Vein Grafts, Dobrin et al., Surgery, pp. 393–400, Mar. 1989.
A New Approach To Mechanical Testing And Modeling Of Biological Tissues, With Application To Blood Vessels, Brossollet et al., Journal of Biomechanical Engineering, vol. 118, pp. 433–439, Nov. 1996.
Mechanical Issues In Vascular Grafting: A Review, Brossollet, The International Journal of Artificial Organs, vol. 15, No. 10, pp. 579–584, 1992.
Essential Physical Characteristics of Vascular Grafts, Chapter 5, Stewart et al., Modern Vascular Grafts.
An Alternate Formulation of Blood Vessel Mechanics and the Meaning of the In Vivo Property, Brossollet et al., J. Biomechanics, vol. 28, No. 6. pp. 679–687, 1995.

On Matching Compliance Between Canine Carotid Arteries and Polyurethane Grafts, Shu et al., Artificial Organs, 21(12): 1247–1254, 1997.
Fourth International Congress Of Biorheology Symposium on Mechanical Properties of Living Tissues, Bauer et al., Biorheology, 19; 409–424, 1982.
New Graft Materials and Concurrent Approaches To An Acceptable Small Diameter Vascular Graft, Yeager et al., Trans Am Soc Artif Intern Organs, vol. XXXIV, pp. 88–94, 1988.
Technique to Control pH in Vicinity of Biodegrading PLA–PGA Implants, Agrawal et al., Orthopaedic Bioengineering, Department of Orthopaedics, pp. 105–114, 1996.
Fibroblast Traction As A Mechanism For Collagen Morphogenesis, Harris et al., Nature, vol. 290, pp. 249–251, 1981.
Culture of Human Endothelial Cells, Jaffe, Transplantation Proceedings, vol. Xii, No. 3, Suppl. 1, pp. 49–53, 1980.
Mechanisms and Dynamics of Mechanical Strengthening In Ligament–Equivalent Fibroblast–Populated Collagen Matrices, Huang et al., Annals of Biomedical Engineering, vol. 21, pp. 289–305, 1993.
The Extracellular Matrix and the Control of Proliferation of Vascular Endothelial and Vascular Smooth Muscle Cells, Gospodarowicz et al., Journal of Supramolecular Structure 13:339–372 (1980).
Fibroblast Behavior on Gels of Type I, III, and IV Human Placental Collagens, Tiollier et al., Experimental Cell Research 191, 95–104 (1990).
Isolation of Putative Progenitor Endothelial Cells for Angiogenesis, Asahara et al., Science, Feb. 14, 1997, vol. 275, pp. 964–967.
Vascular Development: Cellular and Molecular Regulation, Beck Jr., et al., The FASEB Journal, vol. 11, Apr. 1997, pp. 365–373.
Therapeutic Angiogenesis, Takeshita et al., The American Society for Clinical Investigation, Inc. vol. 93, Feb. 1994, pp. 662–670.
Manipulating Angiogenesis, From Basic Science to the Bedside, Pepper, Arteriosclerosis, Thrombosis, and Vascular Biology, vol. 17, No. 4, pp. 605–619, Apr. 1997.
Creation of Viable Pulmonary Artery Autografts Through Tissue Engineering, Shinoka et al., The Journal of Thoracic and Cardiovascular Surgery, vol. 115, No. 3, pp. 536–546, 1998.
Modulation of Cardiac Myocyte Phenotype In Vitro by the Composition and Orientation of the Extracellular Martrix, Simpson et al., Journal of Cellular Physiology 161:89–105 (1994).
Electrospun Fiber Mats: Transport Properties, Gibson et al., Accepted AICHE, Oct. 1998.
Electrospinning Polymer Fibers, Schreuder–Gibson, SSCNC–YM, U.S. Army Natick Research, Development and Engineering Center, 1997.
Neonatal Rat Heart Cells Cultured In Simulated Microgravity, Akins et al., In Vitro Cell. Dev. Biol.—Animal 33:337–334, May 1997.
Microgravity Tissue Engineering, Freed et al., In Vitro Cell. Dev. Biol.—Animal 33:381–385, May 1997.
Three–Dimensional Culture Of Bovine Chondrocytes In Rotating–Wall Vessels, Baker et al., In Vitro Cell. Dev. Biol.—Animal 33:358–365, May 1997.
Skeletal Muscle Satellite Cells Cultured In Simulated Microgravity, Molnar et al., In Vitro Cell. Dev. Biol.—Animal 33:386–391, May 1997.

Myoblast Seeding In A Collagen Matrix Evaluated in vitro, van Wachem et al., Journal of Biomedical Materials Research, vol. 30, 353–360 (1996).

Letter to the Editor, A Simplified Method For Tissue Engineering Skeletal Muscle Organoids in vitro, Shansky et al, In Vitro Cell. Dev. Biol.—Animal 33:659–661, Oct. 1997.

Tissue Engineering Skeletal Muscle: Preparation Of Highly Dense, Highly Oriented Hybrid Muscular Tissues, Okano et al., Cell Transplantation, vol. 7, No. 1, pp. 71–82, 1998.

Hybrid Muscular Tissues: Preparation Of Skeletal Muscle Cell–Incorporated Collagen Gels, Okano et al., Cell Transplantation, vol. 6, No. 2, pp. 109–118, 1997.

Cardiomyocyte Transplantation In A Porcine Myocardial Infarction Model, Watanabe et al., Cell Transplantation, vol. 7, No. 3, pp. 239–246, 1998.

Atomic Force Microscopy Of Structures Produced By Electrospraying Polymer Solutions, Morozov et al., International Journal of Mass Spectrometry 178, pp. 143–149, 1998.

Nanometre Diameter Fibers Of Polymer, Produced by Electrospinning, Reneker et al., Nanotechnology 7, pp. 216–223, 1996.

Collagen Fabrics As Biomaterials, Cavallaro et al, Biotechnology and Bioengineering, vol. 43, pp. 781–791. 1994.

Mechanical Properties of Collagen Fibres: A Comparison Of Reconstituted And Rat Tail Tendon Fibres, Kato et al., Biomaterials, vol. 10, Jan. 1989.

Formation Of Continuous Collagen Fibres: Evaluation Of Biocompatibility And Mechanical Properties, Kato et al., Biomaterials, vol. 11, Apr. 1990.

Regenertion In Grafts Of Normal And Denervated Rat Muscles, Carlson et al., Phlugers Arch, 353, pp. 215–225, 1975.

Isolation And Characterization of Human Muscle Cells, Blau et al., Proc. Natl. Acad. Sci. USA, vol. 78, No. 9, pp. 5623–5627, Sep. 1981.

Formation of Nascent Intercalated Disks Between Grafted Fetal Cardiomyocytes and Host Myocardium, Soonpaa et al., Science, vol. 264, pp. 98–101, 1994.

Skeletal Myoblast Transplantation For Repair of Myocardial Necrosis, Murry et al., The American Society for Clinical Investigation, Inc., vol. 98, No. 11, pp. 2512–2523, Dec. 1996.

Long–Term Survival of AT–1 Cardiomyocyte Grafts In Syngeneic Myocardium, Koh et al., The American Physiological Society, pp. H1727–1733, 1993.

Natural History of Fetal Rat Cardiomyoctes Transplanted Into Adult Rat Myocardial Scar Tissue, Li et al., American Heart Association, Inc., Supplement II Circulation, vol. 96, No. 9, pp. II–179 to II–187Nov. 1997.

In Vivo Survival and Function of Transplanted Rat Cardiomyocytes, Li et al., American Heart Association, Inc., Circulation Research, vol. 78, No. 2, pp. 283–288, Feb. 1996.

Effects of Static Axial Strain on the Tensile Properties and Failure Mechanisms of Self–Assembled Collagen Fibers, Pins et al., University of Medicine and Denistry of New Jersey, Robert Wood Johnson Medical School, pp. 1429–1440, Dec. 22, 1997.

Self–Assembly of Collagen Fibers, Influence of Fibrillar Alignment and Decorin on Mechanical Properties, Pins et al., Biophysical Journal, vol. 73, pp. 2164–2172, Oct. 1997.

Type I Collagen in Solution, Silver et al., The Journal of Biological Chemistry, vol. 255, No. 19, pp. 9427–9433, 1980.

Experimental Investigations of Scaling Laws for Electrospraying: Dielectric Constant Effect, Chen et al., Aerosol Science and Technology, 27:3, pp. 367–380, Sep. 1997.

Electrospraying of Conducting Liquids for Monodisperse Aerosol Generation In the 4 nm to 1.8$\mu$m Diameter Range, Chen et al., Particle Technology Laboratory, Mechanical Engineering Department, University of Minnesota, pp. 963–977, 1995.

Electrospinning Process and Applications of Electrospun Fibers, Doshi et al., Journal of Electrostatics, 35, pp. 151–160, 1995.

Tissue Engineering of Skeletal Muscle, Highly Dense, Highly Oriented Hybrid Muscular Tissues Biomimicking Native Tissues, ASAIO Journal 1997; 43:M749–M753.

Survival of Embryonic Cardiac Myocytes Transplanted Into Host Rat Soleus Muscle, Connold et al., Journal of Muscle Research and Cell Motility 16, 481–489, 1995.

Cell Shape and Growth Regulation In Skeletal Muscle: Exogenous Versus Endogenous Factors, Vandenburgh, Journal Of Cellular Physiology 116:363–371, 1983.

Mechanical Stimulation Of Organogenic Cardiomyocyte Growth in vitro, Vandenburgh et al., The American Physiological Society, pp. c1284–1292, 1996.

Mechanically Induced Orientation Of Adult Rat Cardiac Myocytes In Vitro, Samuel et al., In Vitro Cell. Dev. Biol. 26:905–914, Sep. 1990.

In Vitro Model for Stretch–Induced Hypertrophy of Skeletal Muscle, Vandenburgh, Science, vol. 203, pp. 265–268, Jan. 19, 1979.

Engineering Smooth Muscle Tissue With A Predefined Structure, Kim et al., Department of Chemical Engineering, University Of Michigan, 1997.

Mechanically Induced Alterations In Cultured Skeletal Muscle Growth, Vandenburgh et al., J. Biomechanics, vol. 24, Suppl. I, pp. 91–99, 1991.

Skeletal Muscle Growth Is Stimulated By Intermittent Stretch–Relaxation In Tissue Culture, Vandenburgh et al., American Physiological Society, pp. C674–C682, 1989.

Dynamic Mechanical Orientation Of Skeletal Myofibers In Vitro, Vandenburgh, Developmental Biology 93, pp 438–443, 1982.

Mechanical Forces And Their Second Messengers In Stimulating Cell Growth in vitro, Vandenburgh, American Physiological Society, pp. R350–355, 1992.

Attenuation Of Skeletal Muscle Wasting With Recombinant Human Growth Hormone Secreted From A Tissue–Engineered Bioartificial Muscle, Vandenburgh et al., Human Gene Therapy 9:2555–2564, Nov. 1998.

Optimizing Seeding And Culture Methods To Engineer Smooth Muscle Tissue On Biodegradable Polymer Matrices, Kim et al., Biotechnology And Bioengineering, vol. 57, No. 1, pp. 46–54, 1998.

Highly Oriented, Tubular Hybrid Vascular Tissue For A Low Pressure Circulatory System, Hirai, et al., ASAIO Journal, pp. M383–388, 1994.

Transplantation Of Genetically Marked Cardiac Muscle Cells, Gojo et al., The Journal Of Thoracic and Cardiovascular Surgery, vol. 113, No. 3, pp. 10–18, 1997.

Fibrin gel as a three dimensional matrix in cardiovascular tissue engineering, Ye et al., European Journal of Cardio–thoracic Surgery, 17 (2000) 587–591.

Plasma Concentrate Sealant, PlasmaSeal's Autologous Plasma Concentrate, www.plasmaseal.com/intro.htm, Jun. 14, 2000.

Experimental Suture Of The Peripheral Nerves With Fibrin Glue, Ventura et al., Clinical Orthopaedics, University of Milan.

The Use of Collagen Polymer Tubs and Fibrin Clot in Peripheral Nerve Repair, Chen et al., National Science Council, ROC, Part B: Life Sciences, vol. 18, No. 2, 1994, pp. 58–63.

Exogenous Fibrin Matrix Precursors Stimulant the Temporal Progress of Nerve Regeneration Within a Silicon Chamber, Williams, Neurochemical Research, vol. 12, No. 10, 1987, pp. 851–860.

Fibrinogen and fibrin in strong magnetic fields. Complementary results and discussion, Freyssinet et al., Biochimie, 1984, vol. 66, pp. 81–85.

Effects of fibrin micromorphology on neurite growth from dorsal root ganglia cultured in three–dimensional fibrin gels, Herbert et al., 1998 John Wiley & Sons, Inc., CCC 0021–9304/98/040551–09.

Fibrin Sealant Matrix Supports Outgrowth Of Peripheral Sensory Axons, Zeng et al., Scand J Plast Reconstru Hand Surg. 29: 199–204, 1995.

S. B. Warner, et al., National Textile Center Annual Report, M98–D01, 1(1999).

W. Thumb et al., Spectrochimica Acta 55A, 2729 (1999).

* cited by examiner

PLASMA-DERIVED FIBRIN-BASED MATRICES AND TISSUE

This is a continuation-in-part application of U.S. patent application Ser. No. 09/654,517 filed on Sep. 1, 2000 now abandoned.

FIELD OF THE INVENTION

The present invention relates to novel uses of fibrin, especially plasma-derived fibrin. The invention includes the use of fibrin alone as an extracellular matrix. Further, the invention includes combining anticoagulated plasma, clotting agents and cells together to form engineered tissue. The engineered tissue can include the synthetic manufacture of specific organs or "organ-like" tissue.

BACKGROUND OF THE INVENTION

Fibrin is a natural clotting agent. Therefore, fibrin and fibrin derivatives have commonly been used in hemostatic applications. Its use in analogous applications and in connection with various reinforcing additives has been known and well-documented.

The role of fibrin in the metastatic implantation and growth of cancer cells is also known. Cancer cells are typically highly thrombogenic. This causes rapid clot formation (fibrin formation) around cancer cells and, unfortunately for many cancer patients, very efficiently facilitates the growth of tumors.

In another field, tissue and organ replacement in patients with failing or damaged organ function is hampered by several significant problems. First, the source of replacement tissue or a replacement organ is typically a living related or cadaveric donor. Both of these sources are limited in number and carry the risk of exposing a recipient to pathologic viruses. Second, since the source of the replacement tissue or organ (with the exception of a living identical twin donor) is genetically distinct from the recipient, and the problems of organ rejection and graft versus host disease are significant. Both of these problems can be treated with immunosuppression, but this can cause significant side effects and dramatically increases the risk of infection in a patient.

In a still further field, the emerging techniques with respect to gene transfer can be dangerous when performed in vivo. In other words, in vivo gene transfer can expose a recipient to various complications associated with the processes used to transfer DNA and/or gene sequences into the target cell. Further, there are limitations to known gene therapies, for instance, with respect to engineering viral coats large enough to accept large genes such as the one for Factor VIII (anti-hemophilic factor).

In a still further field of study, the science of chemotherapy for cancer patients is, at least at some level, based on estimates of effectiveness of various treatments in combating a patient's cancer cells. There is no efficient way to identify a patient's cancer cells response to chemotherapy in vivo.

SUMMARY OF THE INVENTION

Accordingly, it is an object of the present invention to overcome the foregoing limitations by providing plasma-derived fibrin as an extracellular matrix. In the fields of tissue and organ replacement specifically, the use of fibrin, and specifically, a patient's own cells and fibrin, could overcome problems of potential infection and rejection. In the field of gene transfer, the manipulation of cells could take place in vitro where cells that are cultured to be inserted into an extracellular matrix comprised of fibrin could be more easily manipulated and tested. Finally, in the context of chemotherapy, the plasma-derived fibrin extracellular matrix implanted with a patient's tumor cells could be used to identify in vitro the susceptibility of those cells to alternative chemotherapy treatments. Each of the foregoing alternatives can result in safer and more predictable medical practices.

In one embodiment, there is provided an extracellular matrix for promoting cell growth comprising anticoagulated plasma and clotting agent The resulting fibrin can be formed of electrospun fibrin fibers or electroaerosol fibrin droplets. Alternatively, the fibrin may be formed of extruded fibrin or sheared fibrin.

In another embodiment, the invention includes an engineered tissue that includes a suspension comprising anticoagulated plasma, clotting agent and cells. The cells may be stem cells and/or committed stem cells. Further alternatively, the suspension may further comprise differentiation inducers, such as DNA sequences (e.g. Myo D to make muscle) or pharmaceuticals (e.g. retonic acid and others). Also, the engineered tissue may have a predetermined shape and the suspension of resulting fibrin and cells has substantially the same predetermined shape.

The invention further includes the method of forming an engineered tissue comprising mixing together anticoagulated plasma, a clotting agent and cells. Additionally, fibrinolytic inhibitors may be added at the time of mixture to prevent degradation of the resulting fibrin matrix before about two days or longer depending on the tissue formed.

In still a further embodiment, the invention includes a method of manufacturing an extracellular matrix. The method includes streaming an electrically-charged solution comprising fibrin onto a grounded target substrate under conditions effective to deposit the fibrin on said substrate to form an extracellular matrix. The electrically charged solution may further comprise fibrinogen and thrombin. Alternatively, the electrically charged solution may comprise plasma and thrombin. The fibrin streamed on to the substrate may comprise either electrospun fibers or electroaerosol droplets.

In still a further embodiment, the invention includes a method for manufacturing an extracellular matrix having a predetermined shape. The method includes preselecting a mold adapted to make the predetermined shape and filling the mold with a suspension comprising fibrin. The suspension may further comprise fibrinogen and thrombin. Alternatively, the method may comprise preselecting a mold adapted to make the predetermined shape wherein the mold comprises a grounded target substrate. Then, an electrically charged solution comprising fibrin is streamed onto the grounded target substrate under conditions effective to deposit the fibrin on the substrate to form the extracellular matrix having the predetermined shape. The fibrin streamed onto the substrate may comprise electrospun fibers or electroaerosol droplets.

In still a further embodiment, a method of manufacturing an engineered tissue comprising fibrin and cells comprises streaming an electrically charged solution comprising the fibrin and cells onto a grounded target substrate under conditions effective to deposit the fibrin and cells onto the substrate. The fibrin and cells streamed onto the substrate may comprise electrospun fibers or electroaerosol droplets. The cells may be stem cells and/or committed stem cells. Alternatively, they may be myoblast cells.

In still a further embodiment, a method is disclosed for manufacturing an extracellular matrix. The method includes an electrically grounded substrate and further providing a plurality of reservoirs containing polymer solutions. The reservoirs are connected substantially at a single orifice that allows the mixture of solutions from the reservoirs upon exit from the reservoirs. The solutions are electrically charged and the mixture of solutions is streamed onto the substrate to form an extracellular matrix. In an alternative embodiment, the plurality of reservoirs comprises first and second reservoirs. The first reservoir has a solution comprising fibrinogen and the second reservoir has a solution comprising thrombin.

In still a further embodiment, the invention includes a method for testing the effectiveness of cancer therapy treatments in vitro. The method includes manufacturing engineered tissue comprising anticoagulated plasma, clotting agent and cancer cells. It further includes preparing a plurality of samples of the engineered tissue and subjecting a plurality of cancer therapy treatments to the samples of engineered tissue. It further includes evaluating the relative effectiveness of the cancer therapy treatments. This method may alternatively include manufacturing engineered tissue by streaming an electrically charged solution comprising fibrin and cancer cells on to a grounded target substrate under conditions effective to deposit the fibrin and cancer cells onto the substrate. Also, the cancer cells may be obtained from a patient who is in need of cancer therapy treatments.

DETAILED DESCRIPTION OF PREFERRED EMBODIMENTS

Figure 1:
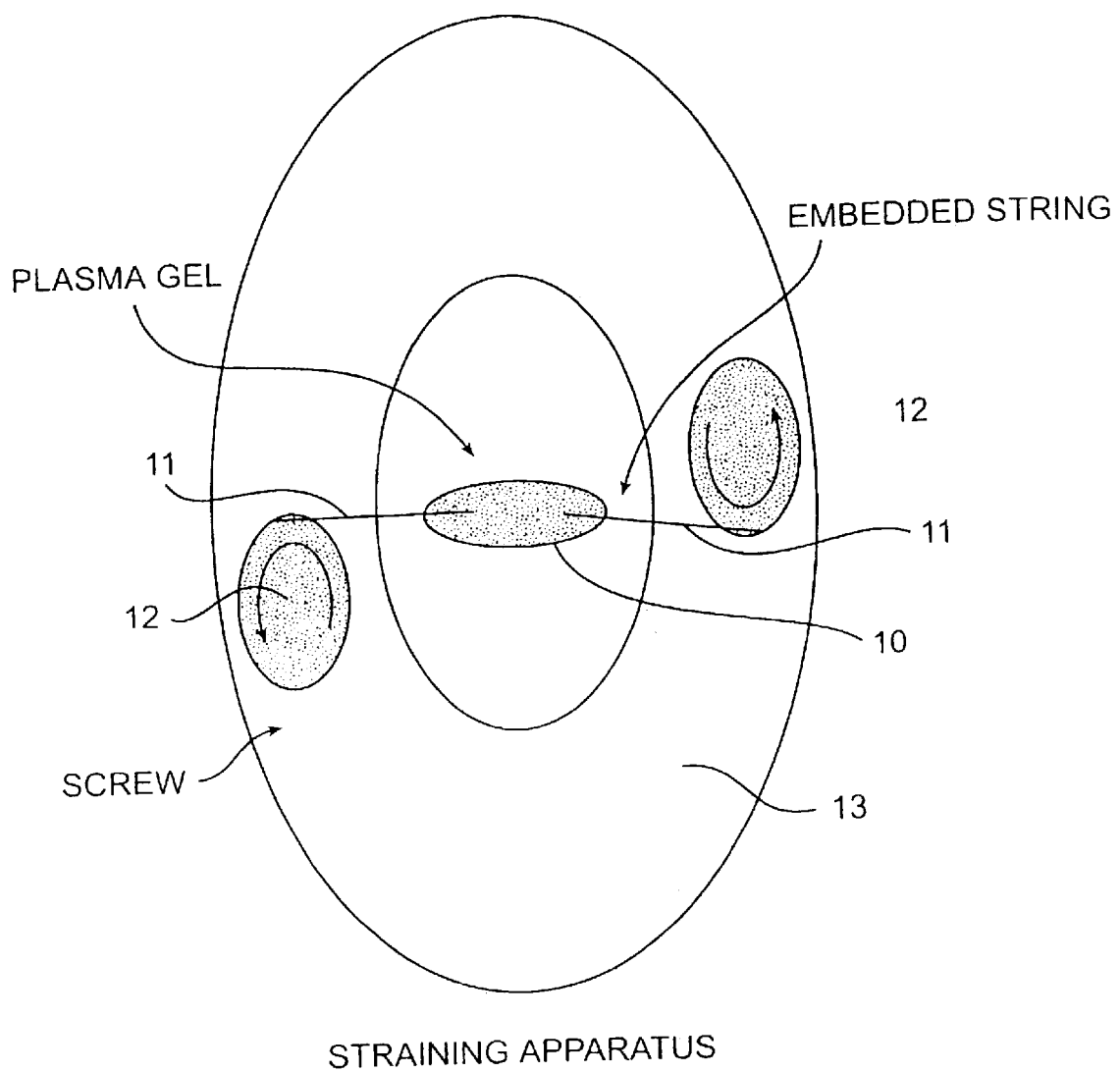
FIG. 1 is a schematic of an apparatus for applying strain to a fibrin clot.

The present invention describes a technique that allows three-dimensional cell growth and tissue/organ synthesis. By mimicking the pathologic process of metastasis, cells are placed in a three-dimensional biological matrix of plasma-derived fibrin to support growth and normal cell to cell interactions. Cells may grow at a rapid rate in these fibrin structures, and may assume the shapes seen in normal tissue and organs.

In very general terms, the mechanism of metastasis is greatly facilitated by the presence of fibrin. When malignant cancer cells detach from a primary tumor, those cells are carried by the lymphatic flow to regional lymph nodes, and then by the circulatory system to distant potential metastatic sites. This is known based on the examination of blood from patients with metastatic disease which reveals circulating tumor cells. These cells are highly thrombogenic. These cells express tissue factor on their surface and thereby initiate the clotting sequence. In other words, tumor cells suspended in normal plasma will cause rapid clot formation. If the cells are put in plasma and then rapidly removed prior to complete clotting of the sample, then the cells are found to be encased in a cocoon of fibrin. This ability to induce fibrin formation is known to be a critical step in the process of metastatic implantation and growth.

In the present invention, normal cells are initially cultured by routine techniques. Once an appropriate cell density has been achieved, the cells are suspended in either solutions of purified fibrinogen or in anticoagulanted plasma. The cell containing suspension is then rapidly mixed with a clotting agent such as thrombin. Fibrin, therefore, is formed in the resulting suspension. This three-dimensional fibrin structure with the cells implanted in it is then returned to a cell culture apparatus for continued growth. As is demonstrated in the following examples, the cells attach to the fibrin network and rapidly concentrate themselves. Depending on the type of cells suspended in the matrix, the cells can be promoted to grow in the same biological appearance as the normal tissue or organ corresponding to the cell type.

A fibrin matrix can also be used to support and grow cells in three dimensions. It is known that cellular morphology is greatly impacted by the environment. Flat substrates such as the bottom of a culture dish typically used for cell work may be unnatural and thus not optimal for growth and proliferation. In this invention, cells will be suspended inside a fibrin matrix and allowed to grow/multiply until a desired state. The fibrin matrix can then be dissolved and the cells recovered for further use. Since the fibrin matrix is easily and specifically degraded, sensitive cells can be released with very little trauma or harm as compared to the traditional trypsin treatment. Furthermore, a fibrin matrix can provide a solid support that can be used to grow tissue at a very high density. One can achieve a favorable density by simply collapsing a fibrin gel either mechanically or chemically. This has advantages if the "growth" phase and "use/service" phase of the cells in question require different cell densities. For instance, growing cells can be made more efficient when more dilute, in terms of nutrient and gas transport. When the growth phase is done, the cells can be concentrated by collapsing the matrix thus providing a concentrated cell "plug" ready for implant or other testing.

A. Fibrin as an Extracellular Matrix

For the purposes of this invention, the term extracellular matrix refers to any three-dimensional structure onto which or in which cells can attach, multiply and grow. Other common terminology for extracellular matrices include scaffold, platform and, for instance, fascial sheath (skeletal muscle).

The use of fibrin as an extracellular matrix has many advantages. As a clotting agent, fibrin is associated with healing in the body. It is a porous medium that allows nutrients and waste to flow to and from cells suspended within a fibrin structure. The presence of fibrin also promotes the growth of vasculature in adjacent regions, and in many other ways is a natural healing promoter.

Fibrin is a readily available material. It is present in plasma. To the extent that the extracellular matrix is being used to fabricate a tissue or organ to be transplanted into a recipient, the recipient's own plasma can be used as a source of fibrin (fibrinogen) to create the matrix. In this way, the matrix is made from a recipient's own fibrin, thereby overcoming any potential complications with respect to viral exposures from materials obtained from other human donors. The recipient will only receive viruses already present in his/her blood. Use of fibrin collected from other sources can be made significantly more safe by multiple purification steps and by processes such as pasteurization. Unfortunately, at this point, the risk of viral infection or other pathogens has not been totally eliminated from such products.

The plasma used preferably includes an anticoagulant such as, but not limited to, sodium citrate, heparin, EDTA, EGTA, hirudin, corn trypsin inhibitor, etc. By using an anticoagulant, and varying the concentration of the anticoagulant, the polymerization of fibrin (i.e., the amount of time to form a fibrin clot) can be regulated. If fibrin is allowed to clot too quickly (approximately less than ten seconds), then the resulting fibrin matrix can be too dense, relatively impermeable, relatively brittle or inflexible, the fibrin fibers too thin, or otherwise undesirable as a scaffold for cellular growth. Alternatively, if the clotting time is greater than approximately ten seconds, and preferably one to several minutes, then the resulting fibrin matrix should have favorable characteristics. The specific anticoagulant concentration required to obtain a desirable clotting time (fibrin matrix formation time) will vary depending on, for instance, the specific anticoagulant used and the concentration of plasma. Of course, the clotting time will also vary through manipulation of additional factors including the concentration of the introduced clotting agent.

Finally, fibrin and especially plasma-derived fibrin is an excellent extracellular matrix because it is eventually absorbed by the body of the recipient and replaced by other naturally-formed extracellular matrices by the cells contained within. In other words, during and after fibrin serves its healing/rebuilding purpose, the body will naturally break it back down through use of other proteins and factors. This is all part of the natural healing mechanism. There would be no lingering foreign matter—only the cells and extracellular matrix constituting the replacement tissue or organ.

B. Building the Extracellular Matrix

In the most simple terms, fibrin is formed by mixing together fibrinogen and thrombin in appropriate concentrations. Plasma-derived fibrin is preferable for many reasons, but any type of fibrin could be used. Building an extracellular matrix comprised of fibrin, therefore, involves different ways of bringing the precursors fibrinogen and thrombin together. It also includes manipulation of the fibrin after it is already formed.

Specifically, a fibrin gel can be formed by mixing together a solution containing fibrinogen with a solution containing thrombin. The particular method of mixture and relative concentrations are known to those skilled in the art. One example of this type of mixture is mixing fibrinogen at 6 mg/ml with thrombin at 2 units/ml in equal volumes to yield 3 mg/ml fibrinogen and one unit/ml thrombin in the final clotting solution. The pH should be held at 7.4 with appropriate buffers, the ionic strength should be 0.15, and the calcium concentration should be 10 mM. By controlling the microenvironment, fibrin can be formed with well defined structural characteristics. That is, the diameter of the fibrin fibers and the size of the spaces between the fibers (pores) is predictable. This being the case, one can engineer fibrin matrices of varying properties by shifting the pH, changing the ionic strength, altering the calcium concentration or adding additional polymeric substrates or cationic materials.

As noted earlier, the use of anticoagulants is one way of slowing down the fibrin clot formation and can, therefore, affect the matrix structure. The clot formation (matrix formation) may also be slowed down by reducing the amount of clotting agents such as calcium and thrombin. The calcium concentration should preferably be 10 mM or less, preferably 3–10 mM. Also, by reducing the thrombin concentration to less than about one unit/ml, the process of clot formation is slowed so that it results in favorable permeability, flexibility and large fiber size. Concentrations of calcium and thrombin used in commercially available fibrin producing products (fibrin glue, fibrin sealant, etc.) are much higher than the ranges noted herein and result in more rapid fibrin formation with resultant, undesirable small pore sizes.

Another way to engineer or modify an extracellular matrix of fibrin is to take a fibrin gel or suspension and mechanically manipulate it. This can be done by a calendaring method to produce a sheet of fibrin. Also, shearing during calendaring, or shearing separately by, for example, by exposing fibrin gel to shear forces between parallel plates, can yield oriented fibrin strands. Alternatively, the fibrin can be extruded to form fibers or tubes of fibrin. It is easy to envision an artificial tendon, for instance, that could be extruded. The only limitations to the mechanical manipulation of fibrin would be that the processing parameters have to be closely monitored so that they would not break down the integrity of the fibrin.

Alternatively, the fibrin can be formed inside a specifically shaped mold. For instance, a particular type of organ or tissue that is desired to be replaced has a specific shape. That shape is then reproduced and created inside a mold designed to mimic that shape. This mold could be filled by forcing the fibrin mechanically into a mold. More preferably, however, the solution of fibrinogen and solution of thrombin are joined together inside the mold or effectively immediately before as they are being injected into the mold. In this way, the fibrin matrix exactly mimics the mold shape. Creating an extracellular matrix that has a specific shape can be very important in creating a new organ. The shape of the matrix can induce cells seeded into the matrix to differentiate in a specific manner. This can result in a more effective, more natural-like organ or tissue being created.

An extracellular matrix of fibrin may also be created through the techniques of electrospinning and electroaerosoling. For the purposes of this discussion, electrospinning and electroaerosoling are terms that are used interchangeably. The difference between them is that the electrospinning technique results in the forming of microfibers, while the electroaerosoling technique will result in the formation of microdroplets. In order to electrospin fibrin, at least two different reservoirs are connected together at an orifice. One of the reservoirs contains fibrinogen, another contains thrombin. The solutions containing these components are mixed together immediately before they are streamed from an orifice in the electrospinning process. In this way, fibrin forms literally as the microfibers or microdroplets are formed in the electrospinning process. Specific details relating to the electrospinning process are explained in greater detail in pending application Ser. No. 09/386,273 and 09/512,081 and in the following examples. Those applications are incorporated by reference as if set forth fully herein.

Finally, an extracellular matrix incorporating fibrin can made by combining fibrin with one or more other materials and components to create a matrix. For instance, it is foreseeable to create an extracellular matrix that has both collagen and fibrin incorporated into it. This could be useful depending on the specific type of tissue or organ being synthesized. For example, the chemical composition of the matrix can also be tailored to specific applications. A fibrin matrix can be induced to form in the presence of other matrix materials. For example, fibrin can be induced to clot as described in the presence of collagen and/or fibronectin and/or laminin and/or other possible matrix constituents. In this way the mechanical and biological properties of the resulting matrix can be modulated. Drugs, other peptides (growth factors), and/or DNA could be trapped in the matrix in a similar fashion for therapeutic applications, for example to promote healing. The matrix composition could also be manipulated after the fibrin has clotted by soaking the matrix in various solutions. For example, the fibrin matrix could be supplemented with other matrix constitutes such as laminin in this fashion.

In addition to mixing fibrin with other matrix ingredients, fibrin can be used in connection with other matrix building processes. In other words, an extruded tube could have an outside layer electrospun onto it wherein the different layers complement each other and provide an appropriate matrix to promote a specific type of cell growth. An example might include a vascular graft comprised of a primarily collagen tube. Outside the tube, an electrospun layer of both fibrin and cells to promote the acceptability of the graft in a particular recipient could be added. A second example might be an in vitro skin preparation formed by growing fibroblasts in one layer, covering the first layer with electrospun collagen, and then growing a second layer composed of epidermal cells in fibrin matrix. This "sandwiching" technique could be used to make a variety of tissues.

C. Treating the Extracellular Matrix

The various properties of the extracellular matrix can be adjusted in accordance with the needs and specifications of the cells to be suspended and grown within it. The porosity, for instance, can be varied in accordance with the method of making the extracellular matrix. Electrospinning a particular matrix, for instance, can be varied by fiber (droplet) size and density. If the cells to be grown in the matrix require a great deal of nutrient flow and waste expulsion, then a very loose matrix could be created. On the other hand, if the tissue to be made requires a very dense environment, then a very tight matrix could be designed.

Particularly with respect to muscle tissue synthesis, it is often desirable to have orientation of the muscle cells. The fibrin can be aligned by mechanically controlling the electrospinning process. It could be aligned by extruding fibers in a specific orientation. The matrix could be oriented in many further ways.

The matrix can also be treated or seeded with various factors and proteins to control the degradation/absorption of the matrix into a recipient environment. For instance, if the cells seeded within the matrix are slow-growing, then it is beneficial to maintain the matrix integrity for a long enough period of time to allow the cells enough time to regenerate and grow. On the other hand, if the cells are able to quickly reproduce and grow, then a short lived matrix could be desirable. Varying the concentration of aprotinin additives, aminocaproic acid, tranxemic acid, or similar fibrinolytic inhibitors or the degree of chemical cross-linking in the matrix could be used to precisely control this variable. The matrix could also be seeded with varying growth factors such as angiogenesis factor to promote a growth of blood vessels upon implantation.

Fibrinolytic inhibitors are important to slow down the degradation/absorption of fibrin particularly when used as a platform for engineered tissue. Without inhibitors, fibrin will break down and disappear in about two days. While this time frame may be acceptable in some applications such as superficial wounds, for instance, more time than two days, preferably weeks or months, is desirable. The inhibitors allow a therapist to match the degradation time with the type of engineered tissue cells, the size of the engineered tissue, the location of implantation, or other relevant parameters. For instance, it is preferable for engineered muscle tissue to have a fibrin matrix support for at least several weeks.

D. Incorporation of Cells to Create Tissue/Organs

The foregoing discussion has been limited to specifics with respect to building an extracellular matrix. In order to actually build tissue or organs (or organ-like tissue), it is necessary to add cells to the matrix. Preferably, the cells are added either before or at the same time as the fibrinogen and thrombin mixtures are brought together. In this way, the cells are suspended throughout the three-dimensional matrix. Typically, the cells are included in the mixture that contains the fibrinogen (whether it is plasma or purified fibrinogen). When the fibrinogen and thrombin are brought together immediately prior to insertion into a mold, or immediately prior to the streaming step in the electrospinning process, the result is a good distribution of cells in suspension in the resulting extracellular matrix.

Many types of cells can be used to create tissue or organs. Stem cells, committed stem cells, and/or differentiated cells may be used. Also, depending on the type of tissue or organ being made, specific types of committed stem cells can be used. For instance, myoblast cells can be used to build various muscle structures. Other types of committed stem cells can be used to make organs or organ-like tissue such as livers, kidneys, etc. As noted earlier, the shape of the extracellular matrix may help send signals to the cells to grow and reproduce in a specific type of desired way. Other factors and differentiation inducers may be added to the matrix to promote specific types of cell growth. Further, there may be different mixtures of cell types that are incorporated into the extracellular matrix. This could be used to enhance, for instance, the vascularization of the resulting "organ" or "organ-like" tissue.

In certain disease states, organs are scarred to the point of being dysfunctional. A classic example is cirrhosis. In cirrhosis, normal hepatocytes are trapped in fibrous bands of scar tissue. With the metagenesis technique described herein, it should be possible to biopsy the diseased liver, obtain viable liver cells, grow them in this new extracellular matrix and re-implant them in the patient as a bridge to or replacement for routine liver transplantations.

Mixing of committed cell lines in a three dimensional matrix can be used to produce structures that mimic complex organs. By growing glucogen secreting cells and insulin secreting cells in separate cultures and then mixing them together in a cell-gel matrix, structures mimicking functional pancreatic beta islets can be produced. These structures could then be placed under the skin or in other locations as implantable, long term treatments for diabetes.

E. Treatment of the Cell/Fibrin Suspension

Once the engineered tissue (cell/fibrin suspension) is put together, the tissue can be immediately inserted into a recipient. Alternatively, the structure can be placed into a culture to enhance the cell growth. Different types of nutrients and growth factors can be added to a culture (or administered to a recipient) in order to promote a specific type of growth of the engineered tissue. In one example, specifically in connection with the preparation of an engineered muscle tissue, the cell/fibrin suspension can be mechanically (actively strained) or passively strained or electrically preconditioned in order to help with the alignment of the cells to form a more functional muscle implant. Passive strain in this context refers to a process in which strain is induced by the cells themselves as they contract and reorganized a matrix. This is typically induced by fixing the ends of the engineered matrix. As the cells contract and alter the matrix the fixed ends of the matrix remain in place and thereby strain the cells as they "pull" against the isometric load. The strain not only aligns the cells, it sends signals to them with respect to growth and development.

The cells/fibrin suspension is also an excellent platform for testing various gene therapies. In other words, by working with the cells/fibrin suspension in vitro, different types of gene therapy and manipulation can be achieved by inserting preselected DNA in the suspension (either the cells, fibrin, plasma, etc.). There is a wider range of therapeutic techniques available in vitro than when techniques are attempted to be administered in vivo. Nonviral techniques such as electroporation may be used to treat the cultured cells prior to insertion into the fibrin matrix. They may also be treated within the fibrin matrix before the engineered tissue is inserted into a recipient. In vitro gene transfer avoids the exposure of a recipient to viral products and other potentially toxic substances associated with gene transfection procedures. In avoids the potential for germ cell line viral incorporation. It avoids the problem of finding or engineering viral coats large enough to accept large genes such as the one for Factor VIII (anti-hemophilic factor). However, in vivo gene therapy may be accomplished by incorporating DNA into the fibrin as it is created, whereby some DNA will be incorporated into the in vivo cells in contact with the fibrin as the fibrin slowly degrades in vivo.

Another useful application of the engineered tissue/organ is that it allows the in vitro culturing of a patient's tumor cells to identify in vitro suspectability to various types of chemotherapy and radiation therapy. In this way, alternative chemotherapy and radiation therapy treatments may be analyzed to calculate the very best treatment for a specific patient. For instance, an engineered tissue may be manufactured that includes fibrin and cancer cells (preferably a patient's own cancer cells). Multiple samples of this tissue can then be subjected to multiple different cancer therapies. The samples may further include other cell lines or additives to better model a given patient and/or therapy. The results can then be directly compared relative to one another.

EXAMPLE 1

CELL CULTURE

Several types of cells are used in experiments with the fibrin and plasma clots:

a) Schwann cells from transgenic mice with truncated SCIP transcription factor. These cells have shown premature and excessive myelination in vivo. This line of cells was selected, because they can be easily cultured in large quantities without any special factor.

b) Primary rat Schwann cells from sciatic nerve. These cells do not divide under the following experimental conditions.

c) Muscle cells of the mouse C2C12 cell line. These cells were selected to demonstrate the feasibility of the method on another type of cells in addition to Schwann cells, and because they can be easily cultured in large quantities without any special growth factor.

In all cases the cells were maintained in 10.5 cm$^2$ plastic culture flasks with Dulbecco's modified pyruvate-free Eagle medium augmented with 10% bovine serum and 1% streptomycin-penicillin (Gibco BRL, Grand Island, N.Y.). The cultures were placed in an incubator at 37 C, 7% Co$_2$ and 100% RH.

Cells type (a) were cultured to confluence then harvested. Cells type (b) were harvested as needed. Cells type (c) were grown in subconfluent cultures for several passages. In order to remove the cells for use, the growth media was drained and the culture was treated aft with 1 mL trypsin-EDTA (Gibco BRL) until the cells detached from the bottom of the dish. The trypsin was then neutralized with 4 mL of fresh media and the content of the flask transferred to a centrifuge tube. The cells were concentrated by centrifugation at 130 g for 5 minutes. The supernatant was removed and the cells resuspended in fresh media to densities of about 106 cells/mL for cell type (a) and (c) and 2–5×10$^5$ cells/mL for cell type (b). These cell suspensions were used in the experiments described as follows.

EXAMPLE 2

Preparation of Thrombin, Fibrinogen and Plasma Stock Solutions

Thrombin was obtained from Baxter as a lyophilized power and dissolved in 10 mM calcium chloride in deionized water to a concentration of 50 units/mL. Alternatively, lyophilized thrombin (Sigma, American Diagnostica, etc.) can be dissolved in 0.15 M NaCl and calcium can be added at the time of clot formation. Blood was obtained by aseptic, nontraumatic venipuncture of a normal volunteer. The blood was collected into blue top vacutainer tubes containing 3.8% sodium citrate. The citrate binding of calcium prevented coagulation of the sample. Platelet poor plasma was prepared by centrifugation at 10,000 g for five minutes. Plasma was decanted from the top of the spun tube leaving the last centimeter depth of plasma on top of the cells to minimize cellular contamination. The citrated platelet poor plasma was filtered through a 0.45 micron filter under sterile conditions to remove fine particulate. Unused portions were stored up to three weeks at 4° C. Fibrinogen was obtained from Sigma as a lyophilized powder and used immediately after dissolution in sterile 10 mM Tris buffer at pH 7.4 and 0.138 M NaCl to a concentration of 3 mg/mL (roughly the concentration in plasma).

EXAMPLE 3

Free Standing Clot (Gel) Formation:

In order to assess the behavior of the cells in clots, a series of experiments was conducted involving different gel densities. To obtain gels with various solids content, the plasma and fibrinogen stock solutions were diluted with cell culture media. Clots were formed from plasma or fibrinogen using:

1) undiluted stock solution 2) 3 parts plasma/fibrinogen solution and 1 part media 3) 1 part plasma/fibrinogen solution and 1 part media The cells suspensions were diluted ten folds with the plasma or fibrinogen solutions. Each hemispherical-shaped clot was formed in a plastic culture dish by combining 45 µL of the diluted cell suspension and 5 µL of stock thrombin solution. The two solutions were mixed gently but swiftly with a pipette and allowed to gel at 37° C. in the incubator for about one hour before covering the clot with media. In order to retard enzymatic degradation of the clot, 10 µL aprotinin (10,000 K.I.U./mL solution) per mL of media was added.

EXAMPLE 4

"Tissue" Formation

Cells are know to adapt to their environment to suit their needs. Both muscle cells a) and c) and Schwann cells self-reorganize fibrin strands into a highly oriented structures. In this experiment the behavior of cells in a fibrin matrix which had been imparted a structure by external mechanical means was studied.

Figure 2:
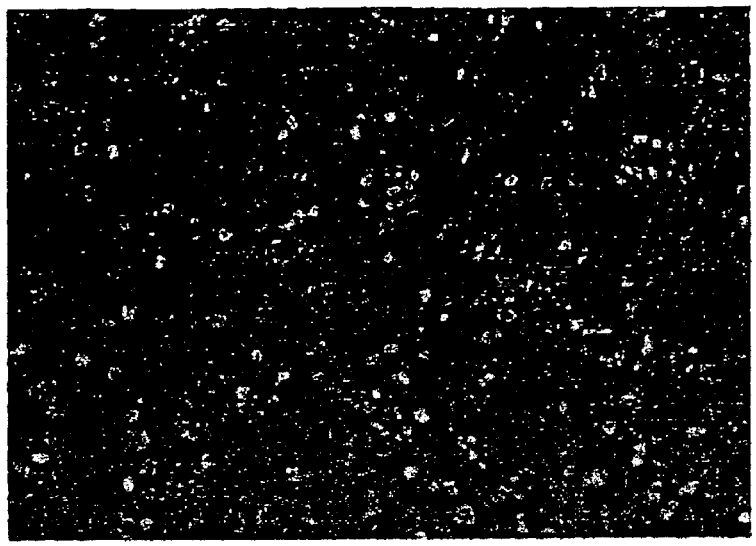
FIG. 2 is a micrograph of a fibrin/cell suspension eight hours after gellation.
Figure 3:
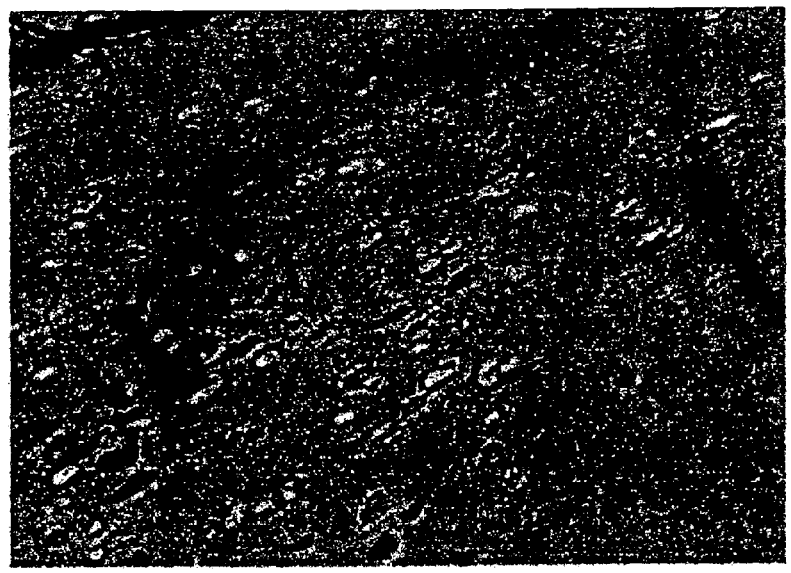
FIGS. 3–5 are micrographs of a suspension of fibrin and cells showing alignment of the cells after 8, 27, and 44 hours of applied strain respectively.
Figure 4:
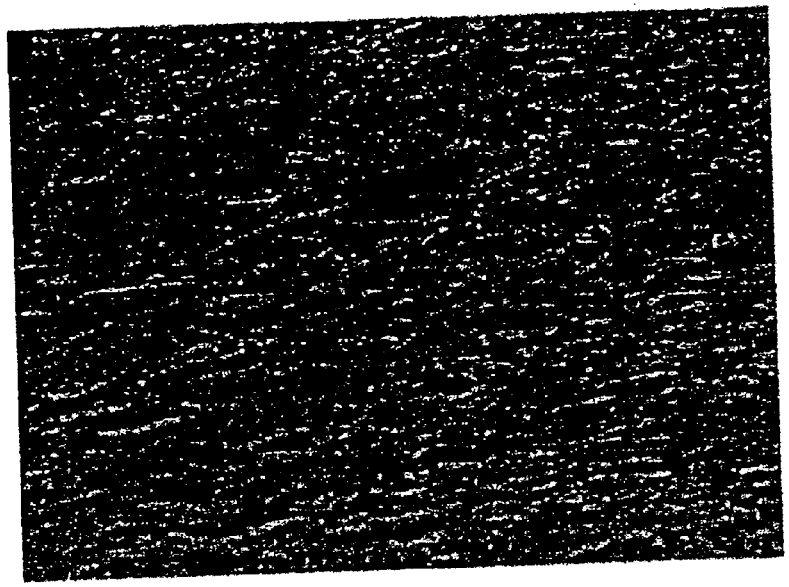
Figure 5:
Figure 6:
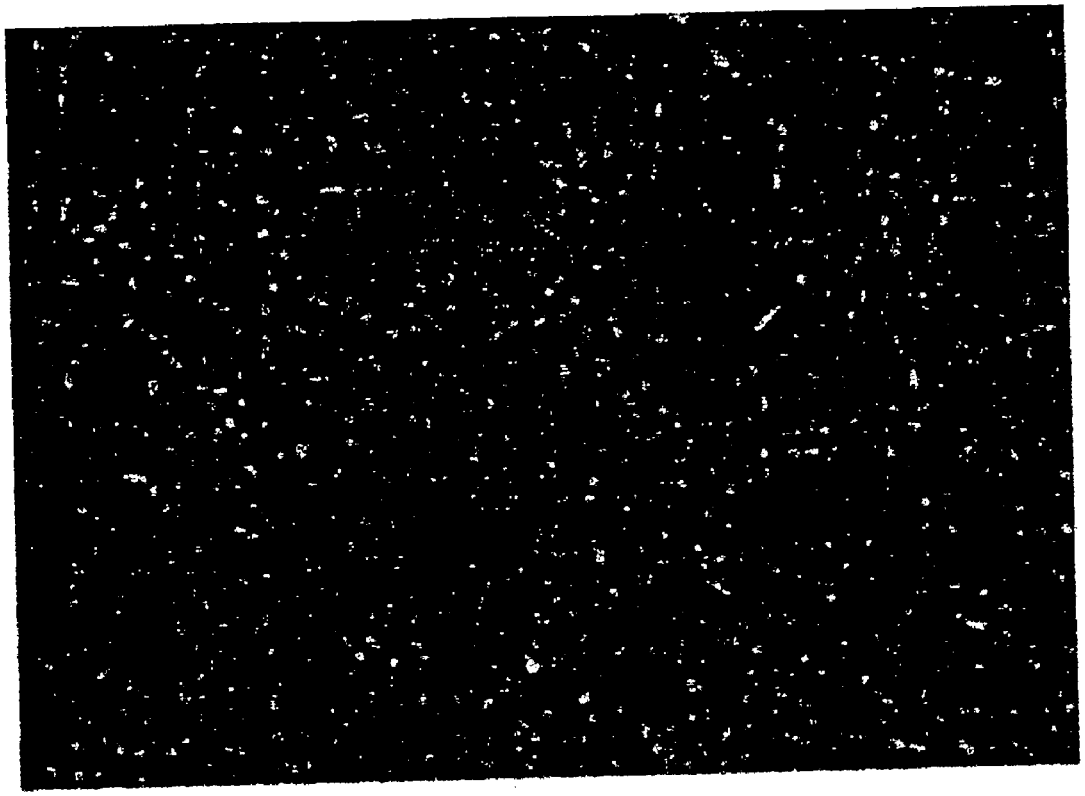
FIG. 6 is a micrograph of a fibrin/cell suspension control sample after 44 hours under no strain.

Cell suspension in 3 parts plasma and 1 part media was prepared using muscle cells c) as described above. The ellipsoid-shaped clot 10 was formed by combining 90 μl of the cells suspension with 10 μL of stock thrombin solution. A short piece of sterile Normex string 11, a stranded polyimid polymer string from Dupont, was embedded within each of the extremities of the clot. Each end of the Normex string 11 was then attached to a set of nylon screws 12 mating with a 5 mm thick polyethylene holder 13. There was sufficient friction between the screws 12 and the holder 13 to prevent any motion once the screws were set. As previously discussed, the clot 10 was allowed to stabilize for one hour in the incubator prior to introducing the media and the aprotinin. Eight hours after gellation (FIG. 2), the Normex strings 11 were tensioned by slightly turning the nylon screws 12 until the fibrin strains in the gel showed alignment under the applied strain. No other adjustments were made to the apparatus for the reminder of the experiment. (See FIGS. 3–5 showing alignment of the cells after 8, 27, and 44 hours respectively.) A control was also performed using the same cells suspension and gelled under the same conditions other than the clot was free standing and not subjected to externally applied strain. (See FIG. 6).

EXAMPLE 5

Figure 7:
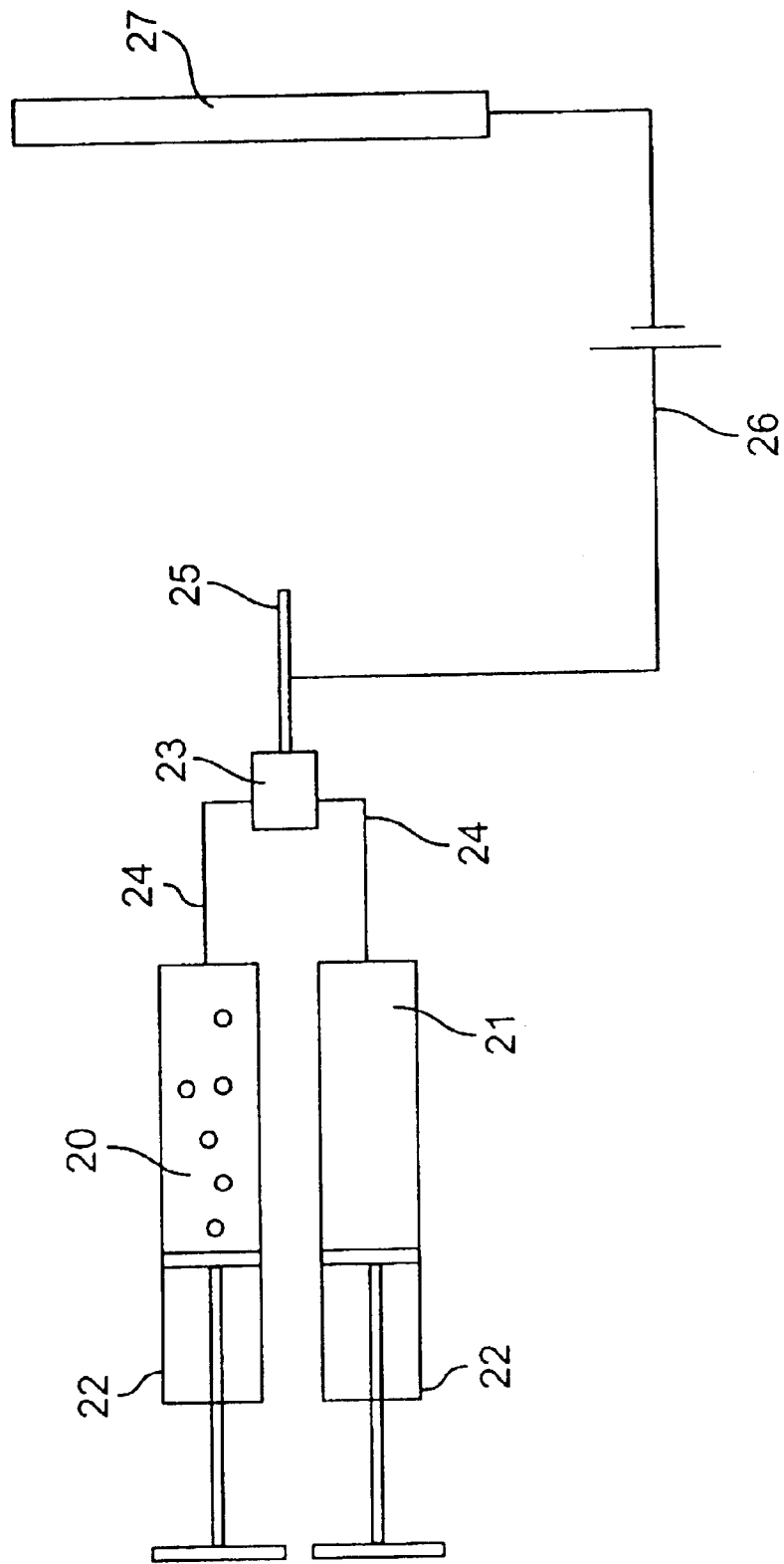
FIG. 7 is a schematic of an electrospinning apparatus.

Electroaerosol/Spin Clots:

Referring to the schematic in FIG. 7, the diluted cells suspension 20 in plain plasma and the stock thrombin solution 21 (~1 mL of each) were loaded into separate 3 mL plastic syringes 22. The syringes 22 were inserted in separate syringe pumps and connected to a mixing tee 23 via a size 13 tygon tube 24. A 27 gauge needle 25 terminated the outlet of the mixing tee. The needle was connected to one pole of a Spellman CZE 1000R high voltage power supply 26. The other pole was connected to a stainless steel foil 27 attached to the back of a plastic culture dish. The mixing tee 23 was placed at about 10 cm from the culture dish. Each of the pumps was set to deliver 1.15 mL/min and a potential of −10 kV was applied, causing fibrin/cell drops to travel from the tip of the needle 25 to the culture dish.

While the invention has been described with reference to specific embodiments thereof, it will understood that numerous variations, modifications and additional embodiments are possible, and accordingly, all such variations, modifications, and embodiments are to be regarded as being within the spirit and scope of the invention.

What is claimed is:

1. Engineered tissue comprising a suspension of anticoagulated plasma, a clotting agent, a fibrinolytic, inhibitor and cells.

2. An engineered tissue as described in claim 1, wherein the cells are stem cells.

3. An engineered tissue as described in claim 2, wherein the stem cells are committed stem cells.

4. An engineered tissue as described in claim 2, wherein the suspension further comprises differentiation inducers.

5. An engineered tissue described in claim 1, wherein the engineered tissue has a predetermined shape and the suspension has substantially the same predetermined shape.

6. An engineered tissue as described in claim 1, further comprising preselected DNA.

7. An engineered tissue as described in claim 6, wherein the preselected DNA is incorporated into the cells.

8. An engineered tissue as described in claim 7, wherein the preselected DNA is incorporated into the cells by using nonviral techniques.

9. A method of manufacturing an engineered tissue comprising mixing cells with anticoagulated plasma and a clot agent, a fibrinolytic inhibitor to form a suspension.

10. The method described in claim 9, wherein the cells are stem cells.

11. The method described in claim 10, wherein the stem cells are committed stem cells.

12. The method described in claim 10, wherein the step of mixing cells with anticoagulated plasma and a clotting agent further comprises mixing in differentiation inducers.

13. The method described in claim 10, further comprising the preliminary step of providing a mold defining a predetermined shape and then mixing the suspension inside the mold.

14. The method described in claim 9, wherein the anticoagulated plasma contains a sufficient concentration of anticoagulates to prevent the resulting fibrin matrix formation from being compete until more than ten seconds after the mixture of anticoagulated plasma, clotting agent, and cells.

15. The method described in claim 9, further wherein the clotting agents have a low enough concentration to prevent the resulting fibrin matrix formation from being complete until more than ten seconds after the mixture of anticoagulated plasma, clotting agent, and cells.

* * * * *